United States Patent [19]

Stein et al.

[11] 4,022,903

[45] May 10, 1977

[54] α-THIENYL AND α-SUBSTITUTED THIENYL, PHENYL AND SUBSTITUTED PHENYL CYCLOPROPYLMETHANOLS USEFUL AS BIODEGRADABLE INSECTICIDES AND MOLLUSICIDES

[75] Inventors: Robert George Stein, Kenosha, Wis.; Terry Lee Couch, Waukegan, Ill.

[73] Assignee: Abbott Laboratories, North Chicago, Ill.

[22] Filed: Dec. 29, 1975

[21] Appl. No.: 644,385

Related U.S. Application Data

[63] Continuation of Ser. No. 584,073, June 5, 1975, abandoned.

[52] U.S. Cl. .......................... 424/275; 424/DIG. 8; 260/332.3 R
[51] Int. Cl.[2] .......................................... A01N 9/12
[58] Field of Search ................................. 424/275

[56] References Cited

UNITED STATES PATENTS

| | | | |
|---|---|---|---|
| 2,329,074 | 9/1943 | Miller | 424/275 |
| 3,238,216 | 3/1966 | Janssen | 260/293.58 |

*Primary Examiner*—V. D. Turner
*Attorney, Agent, or Firm*—Vincent A. Mallare; Robert L. Niblack

[57] ABSTRACT

Biodegradable insecticides and molluscicides having the formula

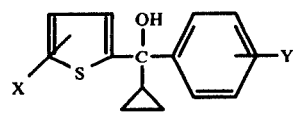

where X is selected from the group consisting of hydrogen, halo, lower alkyl and lower alkoxy; and Y is selected from the group consisting of hydrogen, halo, lower alkyl ($C_1$–$C_8$), lower alkoxy ($C_1$–$C_8$) and halo lower alkyl.

8 Claims, No Drawings

α-THIENYL AND α-SUBSTITUTED THIENYL, PHENYL AND SUBSTITUTED PHENYL CYCLOPROPYLMETHANOLS USEFUL AS BIODEGRADABLE INSECTICIDES AND MOLLUSICIDES

This is a continuation, of application Ser. No. 584,073 filed June 5, 1975, now abandoned.

SUMMARY OF THE INVENTION

The present invention relates to novel α-thenyl and α-substituted thenyl, phenyl and substituted phenyl cyclopropylmethanols useful as biodegradable insecticides and molluscicides and their method of preparation.

The compounds of the present invention are represented by the formula

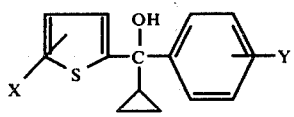

where X is selected from the group of hydrogen, halo, lower alkyl, and lower alkoxy; and Y is selected from the group of lower alkyl, hydrogen, halo, lower alkoxy and halo lower alkyl.

As used herein, the term "halo" means halogens, as illustrated by, but not limited to chlorine, bromine, fluorine and the like.

As used herein, the term "lower alkyl" means saturated-monovalent aliphatic radicals, including straight and branched chain radicals of from 1 to 8 carbon atoms, as illustrated by, but not limited to methyl, ethyl and the like.

As used herein, the term "lower alkoxy" means oxygenous straight and branched chain radicals of from 1 to 8 carbons, as illustrated by, but not limited to methoxy, ethoxy and the like.

BACKGROUND OF THE INVENTION

Many mollusks including snails and slugs, terrestrial as well as aquatic cause serious economic and health problems in many parts of the world. Snails which are members of a large class of gastropod mollusks including most forms having a univalve shell or having no shell can be quite injurious to vegetation as they destroy many varieties of beneficial agricultural plants. Even more harmful is the role that they play in the life cycle of many tropical and semi-tropical diseases. Millions of people and countless animals in many parts of the world are afflicted with these diseases. Snails play a significant role in the growth cycle of the parasite involved in these diseases. In the snails the parasite larval stages develop and emerge to enter warm-blooded animals and mature into worms. The worms in turn lay eggs which are carried to vital organs in the animal or human body by the bloodstream. Lastly, the eggs find their way back to the snails through water supplies and the like and the cycle begins once again. Thus, a single snail can be the ancestor of many millions of new snails per year.

For example, snails of the genre Oncomelania, Australorbis and Bulinus are schistosome intermediate hosts. Likewise, snails of the genre Lymnaea are intermediate hosts for the liver fluke worm. Snails of these genre particularly cause debilitating human problems. Specifically, bilharziasis has long been endemic in various parts of the world, and is even on the increase.

While various control methods of bilharziasis and other diseases of this type have been suggested, the destruction of intermediate snail hosts by toxic chemicals appears to be the most rapid and effective means for reducing transmission of many tropical and semi-tropical diseases.

However, many chemicals useful in combatting mollusks such as snails, such chemicals generically termed as molluscicides, have certain disadvantages. In some cases they are difficult to formulate and in certain types of habitats available formulations do not disperse effectively. In other instances the chemical itself is irritating and potentially dangerous to the handler, is required for use at relatively high dosages, and may be prematurely used up by absorption by soil and organic material. Again, other molluscicides on the market are ineffective at a high pH, are corrosive to equipment or their activity is reduced by bright sunlight. Lastly, some molluscicides while sufficiently active are inactivated at a low pH and/or do not kill snail eggs.

DDT, [1,1,1-trichloro-2-bis(p-chlorophenyl) ethane] has been widely used as an insecticide. However, its usefulness has diminished because of environmental hazards and a low degree of biodegradability.

Thus, continued use of DDT poses an environmental dilemma. Insecticides are required to control vector born diseases and to help protect the food supplies of the world. However, the micropollutants liberated into the environment by DDT threatens both the environment and the existence of many different animals. There is therefore, an urgent need to develop persistent, biodegradable insecticides that would act very much like DDT, but yet, would be rapidly biodegradable and then excreted.

DDT acts as an inducer of microsomal oxidase enzymes in the vertibrate liver. The injurious nature of DDT arises because of the stability of the aryl-chlorine bond, which is not attacked to any extent by the multifunction oxidase of living tissue. Therefore, compounds like DDT are stored in liquid tissues, instead of being metabolized and eliminated from the body. To produce biodegradable analogs, it is necessary to provide sites for attack by multifunctional oxidases.

It has been shown that by attaching "handles" to the DDT molecule, it is possible to obtain biodegradability (Metcalf-Chemtech, Feb. 1972; 105). This biodegradability is produced by the fact that the multifunctional oxidases will attack the "handle", and thus, cause side chain oxidation to carboxylic acids. As a result of these handles, biodegradability is obtained, and thus there is a much less toxic effect than with DDT. With these handles the multifunction oxidases, convert the lipid partitioning substrates of DDT into more water soluble molecules that are excreted from animal bodies, rather than being stored in fatty tissues and concentrated through ecological magnification.

DESCRIPTION OF THE INVENTION

The present invention provides compositions which are effective and persistent insecticides and molluscicides. Yet when such compositions are absorbed into living organisms, they contain one or more points readily susceptible for attack by the MFO enzymes, thus promoting rapid detoxification of the insecticides. Such compositions are readily biodegradable, relatively stable and inexpensive. These compositions are "DDT Type", and have "handles" which are acted upon by the MFO enzymes and thereby are biodegradable or metabolically converted into environmentally accepted products. These compositions also contain an additional route which contributes to its insecticidal activity and/or the relatively low mammalian toxicity exhibited by the compositions of the invention.

It has been found that DDT analogs having the following formula:

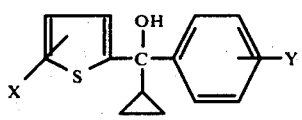

where X is selected from the group of hydrogen, halo, lower alkyl, and lower alkoxy and Y is selected from the group of hydrogen, halo, lower alkoxy, lower alkyl and halo lower alkyl are highly insecticidal and molluscicidal, yet biodegradable when contacted by MFO enzymes, and thus possess low mammalian toxicity.

The inventive compounds were screened for their insecticide and molluscicide activity. Table 1 below outlines results obtained with regard to particular compounds.

To determine activity, the following assays were used.

Leaf Disc Mite Assay

Sample preparation:

A stock solution of 50,000 ppm is prepared. The solution consists of 25 percent DMF, 75 percent IPA and approximately 4 percent Tween 20. The stock solution is diluted (1:20) to a concentration of 2500 ppm using as a diluent 70 percent acetone containing 0.1 percent Tween 20. The 2500 ppm solution is used for the initial screen.

Leaf discs 15 mm in diameter are cut from fresh Henderson Bush Lima Bean plants. Discs are then dropped in the appropriate dilution of the chemical being tested.

The leaf discs are allowed to dry and then placed on moistened filter paper in appropriately labeled petri dishes. Ten adult mites are placed on each disc. Nine discs are used for each compound. Percent mortality is determined after 48 hours.

Compounds producing 80–100 percent mortality are rated very active (VA); a 50–80 percent mortality is rated active (A); 25–50 percent is slightly active (SIA) and less than 25 percent is rated inactive (I). When a compound is rated very active, 1:10 dilutions are made of the 2500 stock. If activity persists, 1:2 dilutions of the 250 ppm solution are screened to determine the $LD_{50}$ of the candidate compound.

The compounds were then screened for their molluscicide activity. Specifically, newly hatched snails of the strain B. glabrata numbering twenty were placed in dechlorinated tap water at a temperature of 26° C. Test chemical was added to the dechlorinated tap water in an amount to provide 10 ppm. After 24 hours exposure to the chemicals the newly hatched snails were then examined for mortality rates.

TABLE I

| No. | X | Y | Calculated Found C | H | bp °/mm | Mites 2500 | ppm 500 | 250 | Mice $L_D50$ mg/kg Orally | Molluscicide Adult ppm 10 | 1 | New ppm 10 | 1 | M.W. | Emp. |
|---|---|---|---|---|---|---|---|---|---|---|---|---|---|---|---|
| 1 | H | Cl | 63.51 63.76 | 4.94 4.98 | 133–137/.08 | SIA | | | | 6/10 | 0/10 | 10/10 | 6/10 | 2.64.8 | $C_{14}H_{13}ClOS$ |
| 2 | H | $CF_3$ | 60.39 59.96 | 4.39 4.49 | 140–143/2.5 | SIA | | | | 6/10 | 0/10 | 10/10 | 4/10 | 298 | $C_{15}H_{13}F_3OS$ |
| 3 | H | $OCH_3$ | 69.21 68.66 | 6.20 6.20 | 155–160/2 | — | | | | 0/10 | 0/10 | 0/10 | 0/10 | 260.3 | $C_{15}H_{16}O_2S$ |
| 4 | Cl | Cl | 56.19 56.20 | 4.04 4.02 | 135–133/2.5 | VA | A | | | 9/10 | 0/10 | 10/10 | 7/10 | 299.2 | $C_{14}H_{12}Cl_2OS$ |
| 5 | Cl | $CF_3$ | 54.14 54.43 | 3.63 3.36 | 145–150/3 | VA | A | | >1000 | 0/10 | 1/10 | 10/10 | 8/10 | 332.2 | $C_{15}H_{12}ClF_3OS$ |
| 6 | Cl | $OCH_3$ | 61.11 61.65 | 5.12 5.14 | 135–140/1 | I | | | >1000 | 5/10 | 0/10 | 10/10 | 0/10 | 294.8 | $C_{15}H_{15}ClOS$ |
| 7 | Cl | $CH_3$ | 64.62 65.21 | 5.42 5.54 | 133–135/1.5 | — | | | >1000 | 9/10 | 0/10 | 10/10 | 4/10 | 278.8 | $C_{15}H_{15}ClOS$ |
| 8 | Cl | Br | 48.91 49.75 | 3.51 3.64 | 175–180/2 | VA | | | | 9/10 | 3/10 | 10/10 | 10/10 | 343.75 | $C_{14}H_{12}BrClOS$ |
| 9 | Cl | F | 59.47 60.59 | 4.27 4.60 | 130–135/1 | — | | | >300 | 9/10 | 0/10 | 10/10 | 5/10 | 282.75 | $C_{14}H_{12}ClFOS$ |

Criteria for assessment of activity
0/10 – 2/10 inactive
3/10 – 7/10 partially active
8/10 – 10/10 active The general mode of synthesis illustrating the method used to obtain the compounds of this group is:

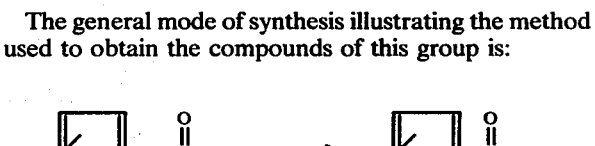

X = hydrogen, halo, lower alkyl, lower alkoxy

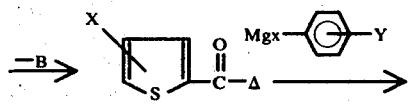

-continued

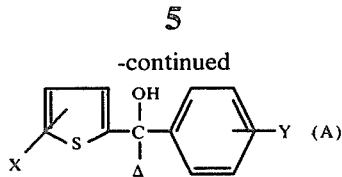

Y = hydrogen, lower alkyl, halo, lower alkoxy, halo lower alkyl

Other routes to the target compounds

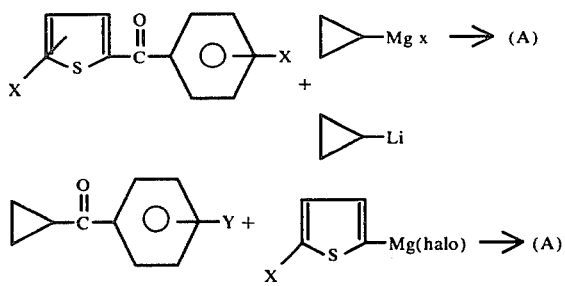

The following examples will serve to illustrate the preparation of the novel compounds used as biodegradable insecticides and molluscicides with low toxicity.

EXAMPLE 1

4-Chloro-(5-Chloro-2-Thienyl)-1-Butanone

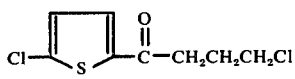

To a stirring solution of 59 g. (0.50 mole) 2-chlorothiophene, α-chlorobutyroylchloride and 500 ml. carbon tetrachloride maintained at 15°–25° C. with the aid of an ice bath was added portionwise 70.5 g. (0.60 mole) of aluminum chloride. The mixture was stirred at room temperature overnight and then carefully poured into 500 ml. of 20% hydrochloric acid solution. The organic layer was separated and washed with sodium bicarbonate solution followed by water. The organic solution was dried over (MgSO$_4$), filtered, and concentrated to an oil under vacuum. The oil was distilled to give 82 g. of material which boiled at 140° C/2 mm. This material solidified on cooling.

Analysis for $C_8H_8Cl_2OS$: C, 43.06; H, 3.61. Found: C, 43.64; H, 3.66.

EXAMPLE 2

Cyclopropyl-5-Chloro-2-Thienyl Ketone

A solution of 82 g. (0.37 mole) 4-chloro-(5-chloro-2-thienyl)-1-butanone in 150 ml. methanol was added to a stirring solution of 22.4 g. (0.40 mole) potassium hydroxide in 300 ml. methanol. The mixture was stirred at 50° C. for 3 hours and at room temperature overnight. The mixture was filtered, and the filtrate was concentrated in vacuo to an oil. The oil was dissolved in either, washed with water, dried, filtered and concentrated in vacuo. The oil distilled at 105°–107° C/2.5 mm. (56 g.)

Analysis for $C_8H_7ClOS$; C, 51.47; H, 3.77. Found: C, 51.72; H, 3.84.

EXAMPLE 3

α-(5-Chloro-2-Thienyl)4-Chlorophenylcyclopropylmethanol

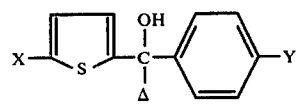

The grignard of 4-bromochlorobenzene was prepared from 1.92 g. (.085 mole) magnesium and 14.3 g. (.075 mole) 4-bromochlorobenzene in 300 ml. ether in the usual manner. A solution of 9.3 g. (0.05 mole) 4-chloro-(5-chloro-2-thienyl)-1-butanone in 100 ml. ether was added to the grignard solution with cooling. The mixture was refluxed 8 hours, cooled and carefully poured into 10% ammonium chloride solution. The layers were separated and the organic phase was washed several times with cold water. The solution was dried over (MgSO$_4$), filtered and concentrated to an oil. The product distilled at 135°–138° C./2.5 mm. 8.6 g. using a Kugelrohr (R. Graeve and G. H. Wahl, Jr. 41, J. Chem. Ed. 279 (1964); available from Aldrich Chem. Co.) distillation apparatus.

Analysis for $C_{14}H_{12}Cl_2OS$: C, 56.19; H, 4.04. Found: C, 56.20; H, 4.02.

EXAMPLE 4

α-Thienyl and α-Substituted Thienyl, Phenyl and Substituted Phenyl Cyclopropylmethanol To a slight excess of (0.12 mole) the appropriately substituted grignard reagent was added (0.10 mole) of the substituted 2-thienyl cyclopropyl ketone in ether. The mixture was refluxed 8 hours, cooled, and carefully poured into a 10% ammonium chloride solution. The layers were separated and the organic phase was washed with cold water and dried over magnesium sulfate. The drying agent was removed and the solution was concentrated in vacuo to an oil. A Kugelrohr distillation gave the desired product. The pertinent physical characteristics of the target compounds are found in Table I.

The compounds of Examples 1 and 2 are intermediates, in which the methods of Close, 79, JAGS, 1455 (1957) were followed.

Representative compounds prepared by the method of Example 4 are:

α-(5-chloro-2-thienyl)-4 trifluoromethylphenylcyclopropylmethanol
α-(5-chloro-2-thienyl)-4 methoxyphenylcyclopropylmethanol
α-(2-thienyl)-4 chlorophenylcyclopropylmethanol
α-(2-thienyl)-4 methoxyphenylcyclopropylmethanol
α-(5-chloro-2-thienyl)-4 methylphenylcyclopropylmethanol Advantageously, the particular new active compounds according to the present invention have strong insecticidal, molluscicidal and acaricidal effects and only a low toxicity towards warm-blooded animals and plants. The effects appear rapidly and are long-lasting. Surprisingly, the instant active compounds have superior activity with respect to insecticidal, molluscicidal and acaricidal activity, and can therefore be used with good results for combatting noxious sucking and biting insects, Diptera and mites (Acarina), and the like.

The sucking insects contemplated essentially include aphids, such as the green peach apid (*Myzus persicae*), the black bean aphid (*Doralis fabae*); Coccidae, such as *Aspidiotus hederae*, *Lecanium hesperidum*, *Pseudococcus maritimus*; Thysanoptera such as *Hercinothrips femoralis*; and bugs, such as the beet bug (*Piesma quadrata*), the bed bug (*Cimex lectularious*); and the like.

The chewing insects contemplated essentially include butterfly larvae, such as *Plutella xylostella*, *Lymantria dispar*; beetles, such as grain weevils (*Sitophilus granarius*), the Colorado beetle (*Leptinotarsa decemlineata*), but also species living in the soil, such as wire worms (*Agriotes sp.*) and cockchafer larvae (*Melolontha melontha*); cockroaches, such as the German cockroach (*Blatella germanica*); Orthoptera, such as the cricket (*Gryllus domesticus*); termites, such as Reticulitermes; Hymenoptera, such as ants; and the like.

The Diptera contemplated particularly comprise the flies, such as the common fruit fly (*Drosophila melanogaster*), the Mediterranean fruit fly (*Ceratitis capitata*), the house fly (*Musca domestica*) and the gnats, such as the mosquito (*Aedes aegypti*); and the like.

The following mites are of particular importance herein: the spider mites (Tetranychus), such as the common spider mite (*Tetranychus urticae*), the fruit tree spider mite (*Paratetranyclus pilosus*) gall mites, such as the red currant gall mite (*Eriophyes ribis*), and tarsonemides, such as *Tursonemus pallidus*; and also ticks; and the like.

These molluscicides are not merely specific against certain distinct mollusks, but will be effective against all snails and slugs, and mollusks generally, including, for example, species of Australois, such as *A. quadelupensis*, species of Bulinus, such as *B. truncatus*, *B. angolensis* and *B. glabraus*, species of Tropicorpus, such as *T. centrimetralis*, species of Limnae, such as *L. natalensis*, *L. bulimoides*, and *L. auricularia*, species of Biophalaria, species of Galba, species of Oncomelania, species of Taphius, such as *T. glabratus*, species of Helisoma such as *H. tribolvis*, species of Pomacea, such as *P. lineata* and *P. glauca*, and species of Ocinebra, such as *O. laponica*.

Significantly, the particular new active compounds of the present invention exhibit an especially good systemic action.

The compositions of the present invention can be formed into any insecticidal formulations using techniques used in the art. Thus, dusts, water, dispersions, emulsions and/or solutions can be formulated by the same methods as DDT insecticides are formulated, provided the carrier solvent is compatable and inert and that it does not react or interfere with the insecticidal and biodegradable characteristics.

While the present invention has been described with reference to illustrative examples, various modifications will be apparent for those skilled in the art, and any such modifications are included within the scope and spirit of this invention as defined by the appended claims.

What we claim is:
1. A method of killing mollusks and insects, comprising applying to said mollusks and insects a lethal amount of a solution of a biodegradable compound having the formula:

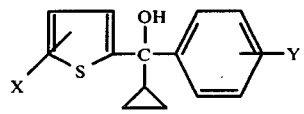

where X is selected from the group consisting of hydrogen, halo, a lower alkyl of 1 to 8 carbon atoms, and a lower alkoxy of 1 to 8 carbon atoms; and Y is selected from the group consisting of hydrogen, halo, lower alkyl, lower alkoxy and halo lower alkyl.

2. The method of claim 1 wherein X and Y are each halo.

3. The method of claim 1 wherein said compound is α-(5-chloro-2-thienyl)-4-chlorophenylcyclopropylmethanol.

4. The method of claim 1 wherein said compound is α-(5-chloro-2-thienyl)-4-trifluoromethylphenylcyclopropylmethanol.

5. The method of claim 1 wherein X is chloro and Y is methoxy.

6. The method of claim 1 wherein said compound is α-(5-chloro-2-thienyl)-4-methoxyphenylcyclopropylmethanol.

7. The method of claim 1 wherein X is hydrogen and Y is halo.

8. The method of claim 1 wherein 1–2500 ppm of the compound of claim 1 is applied to said mollusks and insects.

* * * * *